United States Patent
Shibasaki et al.

(10) Patent No.: US 7,355,061 B2
(45) Date of Patent: Apr. 8, 2008

(54) METHOD OF MANUFACTURING CYANO COMPOUNDS

(75) Inventors: Masakatsu Shibasaki, Mitaka (JP); Motomu Kanai, Tokyo (JP); Yutaka Suto, Tokyo (JP)

(73) Assignee: Takasago International Corporation, Tokyo (JP)

(*) Notice: Subject to any disclaimer, the term of this patent is extended or adjusted under 35 U.S.C. 154(b) by 668 days.

(21) Appl. No.: 10/882,337

(22) Filed: Jul. 2, 2004

(65) Prior Publication Data
US 2005/0004388 A1   Jan. 6, 2005

(30) Foreign Application Priority Data
Jul. 4, 2003   (JP) .............................. 2003-271127

(51) Int. Cl.
*C07C 253/30*   (2006.01)
(52) U.S. Cl. ...................................... 558/339
(58) Field of Classification Search ................. 558/339
See application file for complete search history.

(56) References Cited
OTHER PUBLICATIONS

Suto et al., Direct Catalytic Aldol-Type Reactions Using RCH2CN, Organic Letters, vol. 5, No. 7, pp. 3147-3150, (2003).*
Palomo, Claudio et al., "Fluoride-ion Mediated Reaction Between Trimethylsilylacetonitrile and Carbonyl Compounds. A New Synthesis of β-Trimethylsilyloxy Nitriles," *J. Chem. Soc. Perkin Trans I*, pp. 1692-1694, 1989.
Kisanga, Philip et al., "P(RNCH$_2$CH$_2$)$_3$N-Catalyzed Synthesis of β-Hydroxy Nitriles," *J. Org. Chem.*, 64, pp. 3090-3094, 1999.

* cited by examiner

*Primary Examiner*—James O. Wilson
*Assistant Examiner*—Ebenezer Sackey
(74) *Attorney, Agent, or Firm*—Kubovcik & Kubovcik

(57) ABSTRACT

A method of manufacturing a cyano compound by reacting a carbonyl compound with a nitrile compound having at least one α-hydrogen atom in the presence of a ligand and a metal compound of formula (III),

MX   (III)

wherein M is a copper atom or a silver atom, and X is an alkoxy group, an alkyl group, an aryl group or an anionic residue.

8 Claims, No Drawings

METHOD OF MANUFACTURING CYANO COMPOUNDS

BACKGROUND OF THE INVENTION

1. Field of the Invention

The present invention relates to a method for manufacturing cyano compounds which are useful as intermediates for medicines and agricultural chemicals. Furthermore, the cyano compounds are easily converted to carboxylic acid derivatives which are usable for chemical intermediates such as building blocks of many compounds.

2. Description of the Related Art

At present, many methods of synthesizing cyano compounds have been reported, such as organic syntheses or enzymatic methods. There are many catalytic methods using a cyanide ion as a cyanation reagent, though a catalytic method using a cyanomethyl compound as a cyanomethylation reagent which is reacted with aldehydes and ketones is also known. Examples of the catalytic cyanomethylation reaction are those using trimethylsilylacetonitrile (TMSCH$_2$CN) as a nucleophile (Palomo et al; *J. Chem. Soc. Perkin Trans 1* 1989, 1692), and direct addition of acetonitrile to aldehydes and ketones using proazaphosphatranes as a base catalyst in the presence of magnesium sulfate (Kisanga et al; *J. Org. Chem.* 1999, 64, 3090).

DISCLOSURE OF INVENTION

Accordingly, an object of the present invention is to provide a method of manufacturing cyano compounds with a high yield and a high enantioselectivity.

The present inventors have found that a carbonyl compound and nitrile compound can be reacted in the presence of a specific metal compound and a specific ligand, making it possible to manufacture cyano compounds with a high yield. Furthermore, it was found that by using an optically active compound as ligand, an optically active cyano compound having high optical purity is obtained with sufficient yield, and completed this invention.

Thus the present invention includes the following:

1. A method of manufacturing a cyano compound by reacting a carbonyl compound with a nitrile compound having at least one α-hydrogen atom in the presence of a ligand and a metal compound of formula (III),

MX     (III)

wherein M is a copper atom or a silver atom, and X is an alkoxy group, an alkyl group, an aryl group or an anionic residue.

2. A manufacturing method of 1 above, wherein the carbonyl compound is represented by the formula (I):

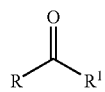

(I)

wherein R and R1 are each independently a hydrogen atom, a hydrocarbon group which may be substituted or a heterocyclic group which may be substituted. However, R and R1 are not simultaneously a hydrogen atom.

3. A manufacturing method of 1 above, wherein the nitrile compound having at least one α-hydrogen atom is represented by the formula (II)

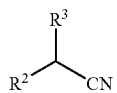

(II)

wherein R2 and R3 are each independently a hydrogen atom, a hydrocarbon group which may be substituted or a heterocyclic group which may be substituted; and the cyano compound is represented by the formula (IV)

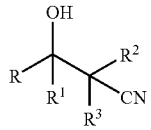

(IV)

wherein R, R1, R2 and R3 are as defined above.

4. A manufacturing method of 3 above, wherein the ligand is a phosphine compound.

5. A manufacturing method of 1 above, wherein the ligand is an optically active bidentate ligand.

6. A manufacturing method of 4 above, wherein the cyano compound represented by the general formula (IV) is an optically active compound.

7. A manufacturing method of 5 above, wherein an optically active bidentate ligand is coordinated to a phosphorous atom or nitrogen atom.

8. A manufacturing method of 7 above, wherein the optically active bidentate ligand is selected from formula (VII), (VIII) or (IX):

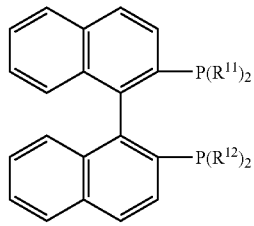

(VII)

wherein R11 and R12 are each independently a cyclopentyl group, a cyclohexyl group, or a phenyl group which may be substituted with an alkyl group, an alkoxy group or a halogen atom;

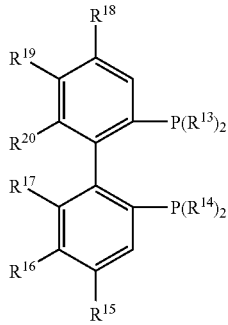

(VIII)

wherein R13 and R14 are each independently a cyclopentyl group, a cyclohexyl group and a phenyl group which may be substituted with an alkyl group, an alkoxy group or a halogen atom; R15, R16, R17, R18, R19 and R20 are each independently a hydrogen atom, an alkyl group, an alkoxy group, an acyloxy group, a halogen atom, a haloalkyl group or a dialkylamino group, with the proviso that R15 and R16, R16 and R17, R18 and R19, and R19 and R20 may form a (poly)methylene group which may be substituted or a (poly)methylenedioxy group; however, R17 and R20 are not simultaneously a hydrogen atom;

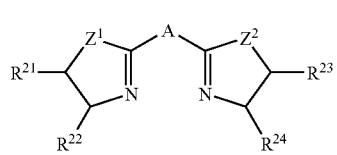

(IX)

wherein at least one of the carbon atoms which is substituted by R21, R22, R23 and R24 is an asymmetric carbon atom; R21, R22, R23 and R24 are each independently a hydrogen atom; an alkyl group having 1 to 6 carbon atoms; an alkylthio group having 1 to 6 carbon atoms; a phenyl group which may be substituted with an alkyl group having 1 to 6 carbon atoms, an alkoxy group having 1 to 6 carbon atoms or halogen atom; or a benzyl group which may be substituted with an alkyl group having 1 to 6 carbon atoms, an alkoxy group having 1 to 6 carbon atoms or halogen atom; (however, R21 and R22 are not simultaneously a hydrogen atom, and R23 and R24 are not simultaneously a hydrogen atom) and, R21 and R22, or R23 and R24 may be combined to form, each, a trimethylene group or a tetramethylene group which may be substituted. Z1 and Z2 are each independently oxygen atom, sulfur atom and a methylene group. A is a methylene group which may be substituted, a phenylene group which may be substituted, a pyridine-2, 6-diyl group which may be substituted, a biphenyl group which may be substituted and a binaphthyl group which may be substituted, and when A is a biphenyl group or a binaphthyl group, these groups may be axially asymmetric.

In the carbonyl compound of formula (I), an example of the hydrocarbon group representative of R and R1 is an alkyl group which may be a linear, branched or cyclic alkyl group having 1 to 15 carbon atoms, or preferably 1 to 10 carbon atoms, or more preferably 1 to 6 carbon atoms. Specific examples of such an alkyl group include methyl group, ethyl group, n-propyl group, isopropyl group, n-butyl group, s-butyl group, isobutyl group, tert-butyl group, n-pentyl group, 2-pentyl group, tert-pentyl group, 2-methylbutyl group, 3-methylbutyl group, 2,3-dimethylpropyl group, n-hexyl group, 2-hexyl group, 3-hexyl group, 2-methylpentyl group, 3-methylpentyl group, 4-methylpentyl group, 2-methylpentan-3-yl group, cyclopropyl group, cyclobutyl group, cyclopentyl group and cyclohexyl group.

These alkyl groups may be substituted with one or two substituents. As each said substituent there is exemplified a hydrocarbon group (1), an aliphatic heterocyclic group (1), an aromatic heterocyclic group (1), an alkoxy group (1), an alkylenedioxy group (1), an aryloxy group (1), an aralkyloxy group (1), a heteroaryloxy group (1), an alkylthio group (1), an arylthio group (1), an aralkylthio group (1), a heteroarylthio group (1), an amino group, a substituted amino group (1), a cyano group, a hydroxy group, a nitro group, a mercapto group, a trialkylsilyl group (1) and a halogen atom.

As the said hydrocarbon group (1), there is exemplified an alkyl group, an alkenyl group, an alkynyl group, an aryl group, an aralkyl group.

The alkyl group as the substituent hydrocarbon group may be a linear, branched or cyclic alkyl group having 1 to 15 carbon atoms, or preferably 1 to 10 carbon atoms, or more preferably 1 to 6 carbon atoms. Specific examples of such an alkyl group include methyl group, ethyl group, n-propyl group, isopropyl group, n-butyl group, s-butyl group, isobutyl group, tert-butyl group, n-pentyl group, 2-pentyl group, tert-pentyl group, 2-methylbutyl group, 3-methylbutyl group, 2,3-dimethylpropyl group, n-hexyl group, 2-hexyl group, 3-hexyl group, 2-methylpentyl group, 3-methylpentyl group, 4-methylpentyl group, 2-methylpentan-3-yl group, cyclopropyl group, cyclobutyl group, cyclopentyl group and cyclohexyl group.

The alkenyl group as the substituent hydrocarbon group may be either a linear or branched chain and is, for example, an alkenyl group having 2 to 15 carbon atoms, or preferably 2 to 10 carbon atoms, or more preferably 2 to 6 carbon atoms. Specific examples of such an alkenyl group include vinyl group, propenyl group, 1-butenyl group, pentenyl group and hexenyl group.

The alkynyl group as the substituent hydrocarbon group may be either a linear or branched chain and is, for example, an alkynyl group having 2 to 15 carbon atoms, or preferably 2 to 10 carbon atoms, or more preferably 2 to 6 carbon atoms. Specific examples of such an alkenyl group include ethynyl group, 1-propynyl group, 2-propynyl group, 1-butynyl group, 3-butynyl group, pentynyl group and hexynyl group.

The aryl group as the substituent hydrocarbon group includes an aryl group having 6 to 14 carbon atoms. Specific examples of the aryl group include phenyl group, naphthyl group, anthryl group, phenanthlyl group and biphenyl group.

The aralkyl group as the substituent hydrocarbon group includes an aralkyl group having 7 to 12 carbon atoms. Specific examples of the aralkyl group include benzyl group, 2-phenylethyl group, 1-phenylpropyl group and 3-naphthylpropyl group.

As the aliphatic heterocyclic group (1), a five- or six-membered aliphatic heterocyclic group, for example, is preferred and there is exemplified an aliphatic heterocyclic group having 2 to 14 carbon atoms containing 1 to 3 hetero atoms such as nitrogen atom(s), oxygen atom(s) and/or sulfur atom(s). Specific examples of the aliphatic heterocyclic group include pyrrolidyl-2-one group, piperidino group, piperazyl group, morpholino group, tetrahydrofuryl group, tetrahydropyranyl group and tetrahydrothienyl group.

As the aromatic heterocyclic group (1), a five- or six-membered mono- or polycyclic aromatic heterocyclic group, for example, is preferred and there is exemplified an aromatic heterocyclic group having 2 to 15 carbon atoms containing 1 to 3 hetero atoms such as nitrogen atom(s), oxygen atom(s) and/or sulfur atom(s). Specific examples of the aromatic heterocyclic group include furyl group, thienyl group, pyridyl group, pyrimidyl group, pyrazyl group, pyridazyl group, pyrazolyl group, imidazolyl group, oxazolyl group, thiazolyl group, benzofuryl group, benzothienyl group, quinolyl group, isoquinolyl group, quinoxalinyl group, phthalazyl group, quinazolyl group, naphthylidyl group, cinnolyl group, benzoimidazolyl group, benzooxazolyl group and benzothiazolyl group.

The alkoxy group (1) may be a linear, branched or cyclic alkoxy group having 1 to 6 carbon atoms. Specific examples of an alkoxy group include methoxy group, ethoxy group, n-propoxy group, isopropoxy group, n-butoxy group, isobutoxy group, 2-butoxy group, tert-butoxy group, n-pentyloxy group, 2-methylbutoxy group, 3-methylbutoxy group, 2,2-dimethylpropyloxy group, n-hexyloxy group, 2-methylpentyloxy group, 3-methylpentyloxy group, 4-methylpentyloxy group, 5-methylpentyloxy group and cyclohexyloxy group.

As the alkylenedioxy group (1), there is exemplified an alkylenedioxy group having 1 to 3 carbon atoms. Specific examples of the alkylenedioxy group include methylenedioxy group, ethylenedioxy group, trimethylenedioxy group and propylenedioxy group.

As the aryloxy group (1), there is exemplified an aryloxy group having 6 to 14 carbon atoms. Specific examples of the aryloxy group include phenyloxy group, naphthyloxy group, anthryloxy group and phenanthryloxy group.

As the aralkyloxy group (1), there is exemplified an aralkyloxy group having 7 to 12 carbon atoms. Specific examples of the aralkyloxy group include benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 1-phenylhexyloxy group, and 6-phenylhexyloxy group.

As the heteroaryloxy group (1), there is exemplified a heteroaryloxy group having 2 to 14 carbon atoms containing 1 to 3 hetero atoms such as nitrogen atom(s), oxygen atom(s) and/or sulfur atom(s). Specific examples of the heteroaryloxy group include 2-pyridyloxy group, 2-pyrazyloxy group, 2-pyrimidinyloxy group and 2-quinoliloxy group.

The alkylthio group (1) may be a linear, branched or cyclic alkylthio group having 1 to 6 carbon atoms. Specific examples of the alkylthio group include methylthio group, ethylthio group, n-propylthio group, isopropylthio group, n-butylthio group, isobutylthio group, 2-butylthio group, tert-butylthio group, pentylthio group, hexylthio group and cyclohexylthio group.

As the arylthio group (1), there is exemplified an arylthio group having 6 to 14 carbon atoms. Specific examples of the arylthio group include phenylthio group, naphthylthio group, anthrylthio group and phenanthrylthio group.

As the aralkylthio group (1), there is exemplified an aralkylthio group having 7 to 12 carbon atoms. Specific examples of the aralkylthio group include benzylthio group, and 2-phenethylthio group.

As the heteroarylthio group (1), there is exemplified a heteroarylthio group having 2 to 14 carbon atoms containing 1 to 3 hetero atoms such as nitrogen atom(s), oxygen atom(s) and/or sulfur atom(s). Specific examples of the heteroarylthio group include 2-pyridylthio group, 4-pyridylthio group, 2-pyrazylthio group, 2-pyrimidinylthio group, 2-benzimidazolylthio group, benzoxazolylthio group, 2-benzothiazolylthio group and 2-quinolilthio group.

As the substituted amino group (1), an amino group in which one or two hydrogen atoms of the amino group are substituted with an alkyl group, an aryl group or an aralkyl group is mentioned.

Specific examples of the amino group substituted with an alkyl group include mono- or dialkylamino group such as N-methylamino group, N,N-dimethylamino group, N,N-diethylamino group, N,N-diisopropylamino group and N-cyclohexylamino group.

Specific examples of the amino group substituted with an aryl group include mono- or di-arylamino group such as N-phenylamino group, N,N-diphenylamino group, N-naphthylamino group, N-naphthyl-N-phenylamino group and N,N-di(p-tolyl)amino group.

Specific examples of the amino group substituted with an aralkyl group include mono- or di-aralkylamino group such as N-benzylamino group and N,N-dibenzylamino group.

The trialkylsilyl group (1) includes, for example, trimethylsilyl group, triethylsilyl group and tert-butyldimethylsilyl group.

The halogen atom includes a fluorine atom, a chlorine atom, a bromine atom and iodine atom.

In the carbonyl compound of formula (I), another example of the hydrocarbon group representative of R and R1 is an alkenyl group which may be a linear, branched or cyclic alkyl group having 2 to 15 carbon atoms, or preferably 2 to 10 carbon atoms, or more preferably 2 to 6 carbon atoms. Specific examples of such an alkenyl group include vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 1-cyclohexenyl group, and 3-cyclohexenyl group.

Also the alkenyl group may be substituted with a substituent, and examples of the substituent include an alkyl group, halogen atom, aryl group and heterocyclic group, specific examples of which are mentioned above.

In the carbonyl compound of formula (I), another example of the hydrocarbon group representative of R and R1 is an alkynyl group which may be a linear or branched alkynyl group having 2 to 15 carbon atoms, or preferably 2 to 10 carbon atoms, or more preferably 2 to 6 carbon atoms. Specific examples of such an alkynyl group include ethynyl group, 1-propynyl group, 2-propynyl group, 1-butynyl group, 2-butynyl group, 3-butynyl group, 1-pentynyl group, 2-pentynyl group, 3-pentynyl group, 4-pentynyl group, 1-hexynyl group, 2-hexynyl group, 3-hexynyl group, 4-hexynyl group and 5-hexynyl group.

Also the alkynyl group may be substituted with substituent, and examples of the substituent include an alkyl group, an aryl group, a heterocyclic group and a trialkylsilyl group, specific examples of which are mentioned above.

In the carbonyl compound of formula (I), another example of the hydrocarbon group representative of R and R1 is an aryl group, which is exemplified by the aryl groups mentioned above. Also these aryl group may be substituted with a substituent, and examples of the substituent include an alkyl group, an aryl group and a heterocyclic group, all specific examples of which are mentioned above.

In the carbonyl compound of formula (I), examples of the heterocyclic group representative of R and R1 are an aliphatic heterocyclic group and an aromatic heterocyclic group, examples of which are mentioned above. Also these heterocyclic groups may be substituted with a substituent, and examples of suitable substituents include an alkyl group, an aryl group and a heterocyclic group, specific examples of which are mentioned above.

In the nitrile compound of formula (II), an example of the hydrocarbon group representative of R2 and R3 is an alkyl group which may be a linear, branched or cyclic alkyl group having 1 to 15 carbon atoms, or preferably 1 to 10 carbon atoms, or more preferably 1 to 6 carbon atoms. Specific examples of such an alkyl group include methyl group, ethyl group, n-propyl group, isopropyl group, n-butyl group, s-butyl group, isobutyl group, tert-butyl group, n-pentyl group, 2-pentyl group, tert-pentyl group, 2-methylbutyl group, 3-methylbutyl group, 2,3-dimethylpropyl group, n-hexyl group, 2-hexyl group, 3-hexyl group, 2-methylpentyl group, 3-methylpentyl group, 4-methylpentyl group, 2-methylpentan-3-yl group, cyclopropyl group, cyclobutyl group, cyclopentyl group and cyclohexyl group.

Also the alkyl group may be substituted with a substituent, and examples of the substituent include a hydrocarbon group, an aliphatic heterocyclic group, an aromatic heterocyclic group, an aryloxy group, an aralkyloxy group, a heteroaryloxy group, an alkylthio group, an arylthio group, an aralkylthio group, a heteroarylthio group, a substituted amino group, a cyano group, a nitro group and a halogen atom, all specific examples of which are mentioned above as examples of the groups R and R1.

In the nitrile compound of formula (II), an example of the hydrocarbon group representative of R2 and R3 is an aryl group, examples of which are mentioned above. Also the aryl group may be substituted with a substituent, and examples of the substituent include an alkyl group, an aryl group and a heterocyclic group, specific examples of which are mentioned above.

In the nitrile compound of formula (II), examples of the heterocyclic group representative of R2 and R3 are an aliphatic heterocyclic group and an aromatic heterocyclic group, examples of which are mentioned above. Also these heterocyclic groups may be substituted with a substituent, and examples of the substituent include an alkyl group, an aryl group and a heterocyclic group, specific examples of which are mentioned above.

The carbonyl compound represented by formula (I) and the nitrile compound represented by formula (II) useful in the present invention include purified or not purified commercially available materials, or can be obtained by known methods.

The following is a description of the ligand used in the present invention.

The preferred ligand for the present invention is a monodentate ligand or bidentate ligand, and the preferred donor atom of the ligand is phosphorous atom or nitrogen atom. A specific example of a monodentate ligand coordinated by phosphorous atom is a trisubstituted phosphine compound represented by formula (V), and a specific example of a bidentate ligand, is a bisphosphine compound represented by general formula (VI).

PR4R5R6                    (V)

R7R8P-Q-PR9R10             (VI)

In formula (V), R4, R5 and R6 are each independently an alkyl group, aryl group or heterocyclic group. And, in formula (VI), R7, R8, R9 and R10 are each independently an alkyl group, aryl group or heterocyclic group, and Q represents a bivalent group.

In the trisubstituted phosphine compound of formula (V) and the bidentate phosphine compound, examples of the alkyl group are a linear, branched or cyclic alkyl group having 1 to 15 carbon atoms, or preferably 1 to 10 carbon atoms, or more preferably 1 to 6 carbon atoms. Specific examples of such an alkyl group include methyl group, ethyl group, n-propyl group, isopropyl group, n-butyl group, s-butyl group, isobutyl group, tert-butyl group, n-pentyl group, 2-pentyl group, tert-pentyl group, 2-methylbutyl group, 3-methylbutyl group, 2,2-dimethylpropyl group, n-hexyl group, 2-hexyl group, 3-hexyl group, 2-methylpentyl group, 3-methylpentyl group, 4-methylpentyl group, 2-methylpentan-3-yl group, cyclopropyl group, cyclobutyl group, cyclopentyl group, cyclohexyl group, methylcyclopentyl group and methylcyclohexyl group.

In the trisubstituted phosphine compound of formula (V), there is exemplified as the aryl group, an aryl group having 6 to 14 carbon atoms. Specific examples of the aryl group include phenyl group, naphthyl group, anthryl group, phenanthlyl group and biphenyl group. Also the aryl group may be substituted with a substituent, and examples of the substituent include an alkyl group, an aryl group and a heterocyclic group, specific examples of which are mentioned above.

In the trisubstituted phosphine compound of formula (V), examples of the heterocyclic group are an aliphatic heterocyclic group or an aromatic heterocyclic group.

As the aliphatic heterocyclic group, a five- or six-membered aliphatic heterocyclic group, for example, is preferred and there is exemplified an aliphatic heterocyclic group having 2 to 14 carbon atoms containing 1 to 3 hetero atoms such as nitrogen atom(s), oxygen atom(s) and/or sulfur atom(s). Specific examples of the aliphatic heterocyclic group include pyrrolidyl-2-one group, piperidino group, piperazyl group, morpholino group, tetrahydrofuryl group, tetrahydropyranyl group and tetrahydrothienyl group.

As the aromatic heterocyclic group, a five- or six-membered mono- or polycyclic aromatic heterocyclic group, for example, is preferred and there is exemplified an aromatic heterocyclic group having 2 to 15 carbon atoms containing 1 to 3 hetero atoms such as nitrogen atom(s), oxygen atom(s) and/or sulfur atom(s). Specific examples of the aromatic heterocyclic group include furyl group, thienyl group, pyridyl group, pyrimidyl group, pyrazyl group, pyridazyl group, pyrazolyl group, imidazolyl group, oxazolyl group, thiazolyl group, benzofuryl group, benzothienyl group, quinolyl group, isoquinolyl group, quinoxalinyl group, phthalazyl group, quinazolyl group, naphthylidyl group, cinnolyl group, benzoimidazolyl group, benzooxazolyl group and benzothiazolyl group.

As the bivalent group represented by Q in the bidentate phosphine compound of formula (VI), examples are alkylene group (2), phenylene group (2), biphenyldiyl group (2) and binaphthalenediyl group (2).

As the alkylene group (2), there is exemplified an alkylene group having 1 to 6 carbon atoms. Specific examples of the alkylene group include methylene group, ethylene group, trimethylene group, tetramethylene group, pentamethylene group and hexamethylene group. The alkylene group may be substituted with a substituent, and examples of the substituent include an alkyl group, an aryl group and a heterocyclic group, specific examples of which are mentioned above.

As the phenylene group (2), there is exemplified a o-, m- or p-phenylene group which may be substituted. Examples of the substituent include an alkyl group, an alkoxy group, hydroxy group, an amino group and a substituted amino group, specific examples of which are mentioned above.

The biphenyldiyl group (2) and binaphthalene group (2) are each optimally a 1,1'-biaryl-2,2'-diyl structured group, and such biphenyldiyl group and binaphthalene group may be substituted with a substituent. Examples of the substituent include an alkyl group, an alkoxy group, hydroxy group, an amino group and a substituted amino group, specific examples of which are mentioned above.

The following is a description of the optically active bidentate ligand.

The preferred optically active bidentate ligand in the present invention is one in which the donor atom of the ligand is phosphorous atom or nitrogen atom. Specifically, optically active bisphosphine compound and optically active bisheterocyclic compound are mentioned.

Optically active bisphosphine compounds were well-known before this application, and as one of them, there is a compound represented by the formula (VII) which has axial asymmetry.

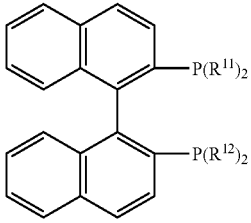

(VII)

In formula (VII), R11 and R12 are each independently a cyclopentyl group, cyclohexyl group, or a phenyl group which may be substituted by an alkyl group, an alkoxy group or a halogen atom.

An example of an alkyl group as a substituent of the phenyl group is a linear or branched alkyl group having 1 to 6 carbon atoms such as methyl group and tert-butyl group. An example of an alkoxy group as a substituent the of phenyl group is linear or branched alkoxy group having 1 to 6 carbon atoms such as methoxy group and tert-butoxy group. Examples of a halogen atom as a substituent of the phenyl group is chlorine atom, bromine atom and fluorine atom. Specific examples of R11 and R12 are phenyl group, p-tolyl group, m-tolyl, 3,5-xylyl group, p-tert-butylphenyl group, p-methoxyphenyl group, p-chlorophenyl group, cyclopentyl group and cyclohexyl group.

The binaphthyl ring of the compound represented by formula (VII) may be substituted with an alkyl group such as methyl group and tert-butyl group; an alkoxy group such as methoxy group and tert-butoxy group; and a trialkylsilyl group such as trimethylsilyl group, triisopropylsiliy group and tert-butyldimethylsilyl group.

Furthermore, as one of the optically active bisphosphine compounds which have axial asymmetry, the bisphosphine compound represented by formula (VIII) is mentioned.

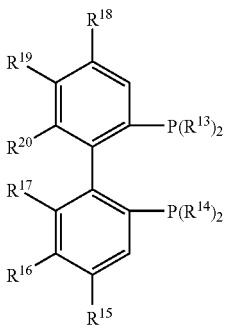

(VIII)

wherein R13 and R14 are each independently a cyclopentyl group, a cyclohexyl group and a phenyl group which may be substituted with an alkyl group, an alkoxy group or halogen atom; R15, R16, R17, R18, R19 and R20 are each independently hydrogen atom, an alkyl group, an alkoxy group, acyloxy group, halogen atom, haloalkyl group and dialkylamino group, with the proviso that R15 and R16, R16 and R17, R18 and R19, and R19 and R20 may form a (poly)methylene group which may be substituted or a (poly)methylenedioxy group which may be substituted; however, R17 and R20 are not simultaneously a hydrogen atom.

An example of an alkyl group as a substituent of the phenyl group is a linear or branched alkyl group having 1 to 6 carbon atoms such as methyl group and tert-butyl group. An example of an alkoxy group as a substituent of the phenyl group is a linear or branched alkoxy group having 1 to 6 carbon atoms such as methoxy group and tert-butoxy group. Examples of a halogen atom as a substituent of phenyl group are chlorine atom, bromine atom and fluorine atom. Specific examples of R13 and R14 are phenyl group, p-tolyl group, m-tolyl, o-tolyl group, 3,5-xylyl group, 3,5-di-tert-butylphenyl group, p-tert-butylphenyl group, p-methoxyphenyl group, p-chlorophenyl group, m-chlorophenyl group, cyclopentyl group and cyclohexyl group.

Examples of R15, R16, R17, R18, R19 and R20 include a linear or branched alkyl group having 1 to 6 cabon atoms, such as methyl group and tert-butyl group; a linear or branched alkoxy group having 1 to 6 carbon atoms, such as methoxy group and tert-butoxy group; an acyloxy group, such as acetoxy group, propanoyloxy group, trifluoroacetoxy group and benzoyloxy group; a halogen atom, such as chlorine atom, bromine atom and fluorine atom; a haloalkyl group having 1 to 4 carbon atoms, such as trifluoromethyl group; and a dialkylamino group, such as dimethylamino group and diethylamino group.

When forming a (poly)methylene group by R15 and R16 or R16 and R17, and forming a (poly)methylene group by R18 and R19 or R19 and R20, a (poly)methylene group having 3 to 5 carbon atoms is preferable, and trimethylene, tetramethylene and pentamethylene groups are specifically mentioned. And, as a substituent on the (poly)methylene group, an alkyl group having 1 to 6 carbon atoms and halogen atom are mentioned.

When forming a (poly)methylenedioxy group by R15 and R16 or R16 and R17, and forming a (poly)methylenedioxy group by R18 and R19 or R19 and R20, a (poly)methylenedioxy group having 3 to 5 carbon atoms is preferable, and methylenedioxy group, ethylenedioxy group and trimethylenedioxy group are specifically mentioned. And, as a substituent on the (poly)methylenedioxy group, an alkyl group having 1 to 6 carbon atoms and halogen atom are mentioned.

Furthermore, 1-(2-(diphenylphosphino)phenyl)-2-isopropyl-2,3-dihydro-1H-phosphindole, bis(2-isopropyl-2,3-dihydro-1H-phosphindole-1-yl)alkane, bis(2-isopropyl-2,3-dihydro-1H-phosphindole-1-yl)arene, 2,2'-bis(diphenylphosphino)-7,7'-(hydrocarbylenedioxy)-1,1'-binaphthyl, 1,1'-biaryl-2,2'-bis(2,5-dimethylphosphol), N,N-dimethyl-1-[1,2-bis(diphenylphosphino)ferrocenyl] ethylamine, 2,3-bis(diphenylphosphino)butane, 1-cyclohexyl-1,2-bis(diphenylphosphino)ethane, 1-phenyl-3,4-bis(diphenylphosphino)pyrrolidine, 2,3-o-isopropylidene-2,3-dihydroxy-1,4-bis(diphenylphosphino)butane, 1,2-bis{(o-methoxyphenyl)phenylphosphino}ethane, 1,2-bis(2,5-dimethylphosphorano)benzene, 1,2-bis(2,5-dimethylphosphorano)ethane, 1-(2,5-dimethylphosphorano)-2-(diphenylphosphino)benzene, 1-(2,5-dimethylphosphorano)-2-(dimethylphenyl)phosphino)benzene, 5,6-bi(diphenylphosphino)-2-norbornene, N,N'-bis(diphenylphosphino)-N,N'-bis(1-phenylethyl)ethylenediamine, 1,2-bis(diphenylphosphino)propane, 2,4-bis(diphenylphosphino)pentane, 4,12-bis(diphenylphosphino)-[2,2]-paracyclophane, 1,1'-bis(2,4-dialkyl-phosphothano)ferrocene, 1-(2-(dialkylphosphino)ferrocenyl) ethyldiphenylphosphine, 1-(2-diphenylphosphino-1-naphthyl)isoquinoline and 2-(2-(2-phenylphosphino) phenyl)-4-(1-methylethyl)-4,5-dihydroxazole is mentioned as other optically active bisphosphines which can be used.

Phosphine ligands which can be used for this invention are not limited to the above.

As an optically active bisheterocyclic compound, a compound represented by formula (IX) is mentioned:

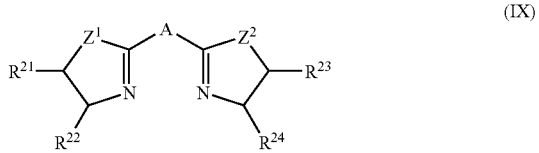

wherein at least one of the carbon atoms which is substituted by R21, R22, R23 and R24 is an asymmetric carbon atom; R21, R22, R23 and R24 are each independently a hydrogen atom; an alkyl group having 1 to 6 carbon atoms; an alkylthio group having 1 to 6 carbon atoms; and a phenyl group which may be substituted with an alkyl group having 1 to 6 carbon atoms, an alkoxy group having 1 to 6 carbon atoms or a halogen atom; or a benzyl group which may be substituted with an alkyl group having 1 to 6 carbon atoms, an alkoxy group having 1 to 6 carbon atoms or a halogen atom; (however, R21 and R22 are not simultaneously a hydrogen atom, and R23 and R24 are not simultaneously a hydrogen atom) and R21 and R22, and R23 and R24 may be combined to form, each, a trimethylene group or a tetramethylene group which may be substituted; Z1 and Z2 are each independently oxygen atom, sulfur atom and a methylene group; A is a methylene group which may be substituted, a phenylene group which may be substituted, a pyridine-2,6-diyl group which may be substituted, a biphenyl group which may be substituted and a binaphthyl group which may be substituted, and when A is a biphenyl group or a binaphthyl group, these groups may be axially asymmetric.

Examples of the alkyl group having 1 to 6 carbon atoms include a linear or branched alkyl group, such as methyl group, ethyl group, isopropyl group and tert-butyl group.

Examples of the alkylthio group having 1 to 6 carbon atoms include a linear or branched alkylthio group, such as methylthio group, isopropylthio group and tert-butylthio group.

Examples of the phenyl group which may be substituted include a phenyl group, a tolyl group, xylyl group, anysyl group and chlorophenyl group.

Examples of the benzyl group which may be substituted include a benzyl group, 1-phenylethyl group, 4-methylbenzyl group, 4-methoxy benzyl group and 4-chlorobenzyl group.

When R21 and R22 together, or R23 and R24 together are combined to form a trimethylene group or tetramethylene which may be substituted, such substituents are an alkyl group and a phenyl group are mentioned above.

When A is a methylene chain, a methylene chain having 1 to 4 carbon atoms is preferable, and, as a substituent on the methylene chain, there may be an alkyl group including a methyl group, ethyl group and tert-butyl group, an alkoxy group including a methoxy group and ethoxy group, and a phenyl group.

Examples of X of the metal compound MX represented by formula (III) used in the present invention are an alkoxy group, an alkyl group, an aryl group and an anionic residue.

The alkoxy group is a linear or branched alkoxy group, for example, methoxy group, ethoxy group, isopropoxy group or tert-butoxy group.

The alkyl group is a linear or branched alkyl group, for example, methyl group, ethyl group or tert-butyl group.

The aryl group is, for example, phenyl group, tolyl group, xylyl group, or mesityl group.

The anionic residue can be selected from an organic or inorganic residue. Examples of such organic residue are an acid radical formed by dissociation of a hydrogen atom as a proton from carboxylic acid or sulfonic acid, etc. Specific examples of such organic residue include acetate, benzoate, trifluoroacetate, methanesulfonate, p-toluenesulfonate and trifluoromethanesulfonate. Specific examples of such inorganic residue include ClO4, BPh4, BF4 and PF6, etc.

As a starting material for preparing the metal compound MX represented by formula (III), a copper or silver compound having plus monovalent is preferred, and a halogen compound is still more preferred. Specific examples of such copper or silver compound include copper chloride (I), copper bromide (I), copper iodide (I), silver chloride, silver bromide and silver iodide.

As the method for producing metal compound MX, for example, in the case M is copper and X is alkoxy group, it can be prepared by reacting a copper compound such as copper chloride mentioned above and alkali metal alkoxide (e.g., sodium alkoxide or potassium alkoxide) as described in the literature (Tsuda et al, J. Am. Chem. Soc., 1972, 94, 658). Accordingly, the obtained copper alkoxide can be purified by sublimation. Moreover it can be also prepared by reacting copper chloride and an aryl or alkyl Grignard reagent, and then reacting with an alcohol according to the method described in the literature (T. Saegusa et al, Inorg. Chem., 1981, 20, 2728). The obtained alkoxide can be used in the present invention with purification or without purification as a solution of the preparation of the alkoxide.

The manufacturing method of the present invention is optimally carried out such that a nitrile compound represented by formula (II) and a carbonyl compound represented by formula (I) are successively added to a solution containing a metal compound represented by formula (III) and a ligand represented by formula (V) to (IX) with stirring at a suitable reaction temperature and time.

Thus, a cyano compound represented by formula (IV) which is an object of the invention can be manufactured.

The cyano compound manufactured by the present invention may be optically active, and, more specifically, may be an optically active compound represented by formula (IV'):

wherein R, R1, R2 and R3 are as defined above. At least one of the two * represents an asymmetric carbon atom.

The present invention is carried out in an atmosphere of an inert gas such as nitrogen or, preferably, argon.

The amount of the nitrile compound represented by formula (II) is 1 to 50 times in moles, preferably 5 to 25 times in moles, the amount of the carbonyl compound represented by formula (I).

The amount of the metal compound represented by formula (III) is 0.1 mol % to 100 mol %, preferably, 1 mol % to 50 mol %, and more preferably, 5 mol % to 30 mol % of the carbonyl compound represented by formula (I).

Correspondingly, the amount of a monodentate ligand represented by formula (V) is 2 to 4 times in moles, and preferably 2.5 to 3.5 times in moles the amount of the metal compound represented by formula (III), and the amount of a bidentate ligand represented by formula (VI), (VII), (VIII) or (IX) is 1 to 3 times in moles, and preferably 1.5 to 2.5 times in moles the amount of the metal compound represented by formula (III).

The method mentioned above for manufacturing the cyano compound is usually carried out in the presence of a solvent inert to the reaction. Any solvent can be used without particular limitation so long as it does not severely inhibit the reaction. Examples of such solvents include amide compounds such as N,N-dimethylformamide, formamide and N,N-dimethylacetoamide, etc.; halogenated hydrocarbons such as dichloromethane, 1,2-dichloroethane, chloroform, carbon tetrachloride and o-dichlorobenzene, etc.; aliphatic hydrocarbons such as pentane, hexane, heptane, octane, decane and cyclohexane, etc.; aromatic hydrocarbons such as benzene, toluene and xylene, etc.; non-nucleophilic alcohols such as tert-butyl alcohol, etc.; ethers such as diethylether, diisopropylether, tert-butylmethylether, dimethoxyethane, ethyleneglycoldiethylether, tetrahydrofuran, 1,4-dioxane and 1,3-dioxolane, etc.; and sulfoxides such as dimethylsulfoxide. Among them, an amide compound such as N,N-dimethylformamide or N,N-dimethylacetoamide and a dimethylsulfoxide are preferably used.

Two or more of these solvents may be suitably combined. Furthermore, an addition of an acid or a base to the reaction mixture may advance a reaction rate and optical purity of the product.

The reaction temperature of the present invention varies depending on the kind of reactant, but the reaction can be usually carried out at temperature in the range of from −30° C. to 80° C., and more preferably from −20° C. to 60° C.

The reaction time of the present invention varies depending on the kind of reactant, but the reaction can be usually carried out in the range of from 0.5 to 100 hours, and more preferably in the range of from 1 to 80 hours.

After completion of the reaction, the reaction mixture obtained is treated by an ordinary method such as neutralization, extraction, evaporation, crystallization, distillation and various types of chromatography, thus an objective cyano compound can be obtained.

DESCRIPTION OF PREFERRED EMBODIMENTS

The following examples further illustrate the present invention in detail but are not to be construed as limiting the scope thereof.

EXAMPLES

NMR spectra were recorded on a JEOL JNM-LA-500 spectrometer, operating at 500 MHz for 1H-NMR, 125.65 MHz for 13C NMR, and 470.4 MHz for 19F NMR. Chemical shifts were reported downfield from tetramethylsilane for 1H-NMR.

The enantiomeric excess (ee) and the diastereomeric rate (de) were determined by HPLC analysis.

column: CHIRALCEL OJ-H (DAICEL CHEMICAL INDUSTRIES, LTD.),

CHRALPAK AS-H (DAICEL CHEMICAL INDUSTRIES, LTD.)

Example 1

Synthesis of 3-hydroxy-2-methyl-3-phenylpropionitrile

Under an argon atmosphere, CuO(tert-Bu) (0.03 mmol, 60 µL in THF) and 1,2-bis(diphenylphosphino)ethane (hereinafter, referred to as dppe) (18 mg, 0.045 mmol) were mix dried under vacuum for 1 hour. To the residue, dimethylsufoxide (hereinafter, referred to as DMSO) (0.3 mL), propionitrile (0.3 mL), and benzaldehyde (30 µL, 0.3 mmol) were added to start the reaction. After 2 hours, saturated ammonium chloride was added, and the product was extracted with ethyl acetate. The combined organic layer was washed with saturated brine, and dried over sodium sulfate. Filtration, evaporation, and purification by silica gel column chromatography (ethyl acetate/hexane=1/3) gave the product in 90% yield (44 mg). A diastereomeric rate of the obtained compound was determined to be 1.5:1 (syn:anti).

1H-NMR(CDCl3) δ: syn body 1.23(d, J=7.1 Hz, 3H), 2.64 (brs, 1H), 2.97(dq, J=5.8, 7.1 Hz, 1H), 4.77(brd, J=5.8 Hz, 1H), 7.35(m, 5H) anti body 1.20(d, J=7.0 Hz, 3H), 2.72(brs, 1H), 2.88(dq, J=6.4, 7.0 Hz), 4.67(brd, J=6.4 Hz, 1H), 7.35(m, 5H)

Example 2~Example 13

Direct Catalytic Addition of Alkylnitriles

Reaction conditions of the direct catalytic addition were carried out at room temperature in the presence of CuO(tert-Bu) and various phosphine ligands nitrites and carbonyl compounds in a similar manner to Example 1. The results are shown in Table 1 below. The term "mol %" corresponds to a molar quantity of the carbonyl compound of the general formula (I). The codes in Table 1 represent the following:

Ph: phenyl group, Cy: cyclohexyl group, i-Bu: isobutyl group, Et: ethyl group, DMF: N,N-dimethylformamide Diastereomeric rate in Example 13 was determined to be 1.6:1 (syn:anti).

TABLE 1

| Example No. | R1 | R2 | R3 | CuO(tert-Bu) (mol %) | Ligand | (mol %) | solvent | time (hr) | yield (%) |
|---|---|---|---|---|---|---|---|---|---|
| 2 | Ph | H | H | 10 | PPh3 | (30) | THF | 48 | 27 |
| 3 | Ph | H | H | 10 | P(n-Bu)3 | (30) | THF | 48 | 34 |
| 4 | Ph | H | H | 10 | PCy3 | (30) | THF | 48 | 34 |
| 5 | Ph | H | H | 10 | PCy3 | (30) | DMF | 3 | 68 |
| 6 | Ph | H | H | 10 | PCy3 | (30) | tert-BuOH | 3 | 54 |
| 7 | Ph | H | H | 10 | dppe | (15) | DMF | 6 | 95 |
| 8 | Ph | H | H | 10 | dppe | (15) | DMSO | 2 | 95 |
| 9 | Ph | H | H | 5 | dppe | (7.5) | DMSO | 6 | 81 |

TABLE 1-continued

| Example No. | R1 | R2 | R3 | CuO(tert-Bu) (mol %) | Ligand | (mol %) | solvent | time (hr) | yield (%) |
|---|---|---|---|---|---|---|---|---|---|
| 10 | Ph—CH=CH— | H | H | 10 | dppe | (15) | DMSO | 2 | 78 |
| 11 | Cy | H | H | 10 | dppe | (15) | DMSO | 2 | 71 |
| 12 | i-Bu | H | H | 10 | dppe | (15) | DMSO | 2 | 71 |
| 13 | Ph | Et | H | 10 | dppe | (15) | DMSO | 4 | 76 |

Example 14

Synthesis of Optically Active 3-hydroxy-4,4-dimethyl-5-phenylpentanenitrile

Under an argon atmosphere, (R)-DTBM-SEGPHOS (53.1 mg, 0.045 mmol) and CuO(tert-Bu) (60 μL of 0.5 molar THF solution, 0.03 mmol) were mixed and the solvent was evaporated under vacuum. The residue was dried under vacuum for 1 hour. DMF (0.3 mL) and acetonitrile (0.3 mL) were added, and the mixture was cooled in an ice bath. 2,2-dimethyl-3-phenylpropionaldehyde was added and the mixture was stirred for 48 hours at 4° C. Saturated aqueous ammonium chloride was added and the product was extracted with ethyl acetate. The combined organic layer was washed with saturated brine and dried over sodium sulfate. Filtration, evaporation, and purification by silica gel column chromatography (ethyl acetate/hexane=1/3) gave the product in 45% yield (27.4 mg). The ee was determined to be 53% ee and absolute configuration of this compound was (R) configuration.

1H-NMR(CDCl3) δ: 0.93(s, 3H), 1.01(s, 3H), 2.58(m, 4H), 2.82(d, J=13.2 Hz, 1H), 3.77(dd, J=3.1, 9.5 Hz, 1H), 7.23(brd, J=7.3 Hz, 2H), 7.3-7.38(m, 3H) 13C-NMR: 21.63, 21.65, 23.21, 38.68, 44.51, 73.55, 119.03, 126.35, 128.03, 130.56, 137.59

DTBM-SEGPHOS: (4,4'-bi-1,3-benzodioxole)-5,5'-diyl-bis(bis(3,5-di-tert-butyl-4-methoxyphenyl)phosphine)

Example 15

Synthesis of (R)-3-hydroxy-3-(4-methylphenyl)propanenitrile

The title compound was obtained in a similar manner to Example 14 except for 4-methylbenzaldehyde being used instead of 2,2-dimethyl-3-phenylpropionaldehyde. (Yield: 74%, 48% ee). 1H-NMR(CDCl3) δ: 2.36(s, 3H), 2.48(brs, 1H), 2.74(m, 2H), 5.02(brt, J=6.0 Hz, 1H), 7.19(d, J=11.6 Hz, 2H), 7.30(d, J=11.6 Hz, 2H)

Example 16

Synthesis of Optically Active 3-hydroxynonanenitrile

Under an argon atmosphere, to a 0.25M CuO(tert-Bu) THF solution (200 μL, 0.05 mmol) was added (R)-DTBM-SEGPHOS (88.5 mg, 0.075 mmol) and stirred for 30 min at room temperature. The solvent was removed in vacuo, HMPA (1.0 mL), acetonitrile (500 μL) was added and then 1-heptanal was added dropwise over 5 hours. After 5 min, saturated ammonium chloride was added and extracted with ethyl acetate (4×10 mL). The combined organic layer was dried over sodium sulfate and then removed the drying agent by filtration. The solvent was evaporated under reduced pressure, and the residue was purified by silica gel column chromatography (ethyl acetate:n-hexane=1:10) to afford 3-hydroxynonanenitrile (72.1%, 74% ee).

Example 17

Synthesis of Optically Active 3-hydroxyundecanenitrile

The title compound was obtained in a similar manner to Example 16 except for 1-nonanal being used instead of 1-heptanal. (yield: 62%, 73% ee).

Example 18

Synthesis of Optically Active 3-cyclohexyl-3-hydroxypropanenitrile

The title compound was obtained in a similar manner to Example 16 except for cyclohexanecarboxaldehyde being used instead of 1-heptanal. (yield: 91%, 75% ee).

Example 19

Synthesis of Optically Active 3-hydroxy-5-methylhexanenitrile

The title compound was obtained in a similar manner to Example 16 except for isovaleraldehyde being used instead of 1-heptanal. (yield: 86%, 75% ee).

Example 20

Synthesis of Optically Active 3-hydroxy-5-phenylpentanenitrile

The title compound was obtained in a similar manner to Example 16 except for hydrocinnamaldehyde being used instead of 1-heptanal. (yield: 67%, 68% ee).

INDUSTRIAL APPLICABILITY

An objective compound of the present invention is useful as an intermediate of medicines or agricultural chemicals. Furthermore, an objective compound of the present invention is useful as an intermediate of carboxylic acid as a building block of many compounds.

The invention claimed is:

1. A method of manufacturing a cyano compound comprising reacting a carbonyl compound with a nitrile compound having at least one α-hydrogen atom in the presence of a ligand and a metal compound of formula (III), $$MX \qquad (III)$$

wherein M is a copper atom or a silver atom, and X is an alkoxy group, an alkyl group, an aryl group or an anionic residue.

2. The method of claim 1, wherein the carbonyl compound is represented by formula (I):

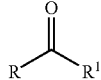
(I)

wherein R and R1 are each independently a hydrogen atom, a hydrocarbon group which may be substituted or a heterocyclic group which may be substituted, with the proviso that R and R1 are not simultaneously a hydrogen atom.

3. The method of claim 1, wherein the nitrile compound having at least one α-hydrogen atom is represented by formula (II)

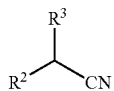
(II)

wherein R2 and R3 are each independently a hydrogen atom, a hydrocarbon group which may be substituted or a heterocyclic group which may be substituted;
and, the cyano compound is represented by formula (IV)

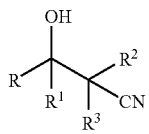
(IV)

wherein R, R1, R2 and R3 are as defined above.

4. The method of claim 3, wherein the ligand is a phosphine compound.

5. The method of claim 1, wherein the ligand is an optically active bidentate ligand.

6. The method of claim 4, wherein the cyano compound represented by formula (IV) is an optically active compound.

7. The method of claim 5, wherein the optically active bidentate ligand is coordinated by a phosphorous atom or nitrogen atom.

8. The method of claim 7, wherein the optically active bidentate ligand is selected from formula (VII), (VIII) or (IX):

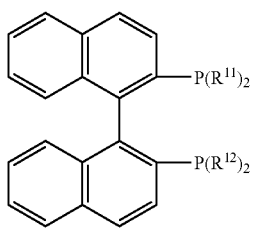
(VII)

wherein R11 and R12 are each independently a cyclopentyl group, a cyclohexyl group, or a phenyl group which may be substituted by an alkyl group, an alkoxy group or a halogen atom;

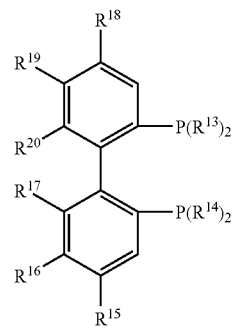
(VIII)

wherein R13 and R14 are each independently a cyclopentyl group, a cyclohexyl group or a phenyl group which may be substituted with an alkyl group, an alkoxy group or a halogen atom; R15, R16, R17, R18, R19 and R20 are each independently hydrogen atom, an alkyl group, an alkoxy group, an acyloxy group, a halogen atom, a haloalkyl group or a dialkylamino group, with the proviso that R15 and R16, R16 and R17, R18 and R19, and R19 and R20 may form a (poly)methylene group which may be substituted or a (poly)methylenedioxy group which may be substituted; with the proviso that R17 and R20 are not simultaneously a hydrogen atom

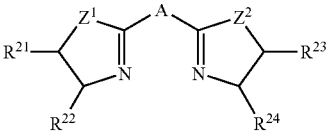
(IX)

wherein at least one of the carbon atoms which is substituted by R21, R22, R23 and R24 is an asymmetric carbon atom; R21, R22, R23 and R24 are each independently a hydrogen atom; an alkyl group having 1 to 6 carbon atoms; an alkylthio group having 1 to 6 carbon atoms; and a phenyl group which may be substituted with an alkyl group having 1 to 6 carbon atoms, an alkoxy group having 1 to 6 carbon atoms or halogen atom; or a benzyl group which may be substituted with an alkyl group having 1 to 6 carbon atoms, an alkoxy group having 1 to 6 carbon atoms or halogen atom; provided, however, that R21 and R22 are not simultaneously a hydrogen atom, and R23 and R24 are not simultaneously hydrogen atom; and R21 and R22, R23 and R24 may be combined to form, each, a trimethylene group or a tetramethylene group which may be substituted; Z1 and Z2 are each independently oxygen atom, sulfur atom and a methylene group; A is a methylene group which may be substituted, a phenylene group which may be substituted, a pyridine-2,6-diyl group which may be substituted, a biphenyl group which may be substituted or a binaphthyl group which may be substituted, and when A is a biphenyl group or a binaphthyl group, this group may be axially asymmetric.

* * * * *